United States Patent [19]
Klever et al.

[11] Patent Number: 5,836,339
[45] Date of Patent: Nov. 17, 1998

[54] RAINDROP COUNTER AND CONTROL SYSTEM FOR IRRIGATION SYSTEMS

[76] Inventors: David L. Klever, 2400 Lakeview Ave. #1, Richmond, Va. 23220; M. Thomas Craigo, 8753 Signal Hill Rd. #4, Manassas, Va. 20110

[21] Appl. No.: 774,407

[22] Filed: Dec. 31, 1996

[51] Int. Cl.$^6$ .................................................. F16K 31/02
[52] U.S. Cl. .............................. 137/78.2; 137/624.12; 239/69; 239/70
[58] Field of Search ................ 239/69, 70; 137/624.12, 137/78.2

[56] References Cited

U.S. PATENT DOCUMENTS

| | | | |
|---|---|---|---|
| 3,808,385 | 4/1974 | Klinefelter | 200/61.04 |
| 4,613,764 | 9/1986 | Lobato | 307/116 |
| 4,684,920 | 8/1987 | Reiter | 340/310 |
| 4,701,613 | 10/1987 | Watanabe | 250/227 |
| 4,919,165 | 4/1990 | Lloyd | 137/78.2 |
| 4,921,001 | 5/1990 | Pittsinger | 137/78.2 |
| 4,987,296 | 1/1991 | Kajioka | 250/222.1 |
| 5,004,014 | 4/1991 | Bender | 137/624.12 |
| 5,060,859 | 10/1991 | Bancroft | 239/64 |
| 5,193,570 | 3/1993 | Mott | 137/78.2 |
| 5,207,380 | 5/1993 | Harryman | 239/64 |
| 5,321,578 | 6/1994 | Morrison | 361/178 |
| 5,355,122 | 10/1994 | Erickson | 340/602 |
| 5,375,617 | 12/1994 | Young | 137/78.3 |
| 5,445,176 | 8/1995 | Goff | 137/80 |
| 5,464,044 | 11/1995 | Brinkerhoff | 137/78.3 |
| 5,546,974 | 8/1996 | Bireley | 137/78.3 |

OTHER PUBLICATIONS

Jul./Aug. 1994 Irrigazette "Equipment on the Market" (J.F. Leblond).

May/Jun. 1995 Electronic House "Intelligent Sprinklers" (L. Montgomery).

*Primary Examiner*—A. Michael Chambers

[57] ABSTRACT

Disclosed is a raindrop counter and control system for irrigation systems which provides the quick detection of the presence, and subsequent absence of precipitation once it has first been detected. When applied to automatic irrigation systems and the like, the invention disables normal operation of the system by interrupting power to the irrigation valves during and after detection of precipitation. The control system includes sensitivity selections to electronically adjust the triggering threshold to precipitation, as well as a decoupled comparator network which compensates for background ambient light levels. Furthermore, the duration of sensed precipitation will determine the disable time period by reprogramming the output delay from a short to a long delay time period, if so desired. The time of the long delay is then user selectable to a plurality of time periods. The invention comprises a small outdoor probe, and a separate control and display unit that is capable of interfacing with a plurality of automated systems.

3 Claims, 8 Drawing Sheets

RAINDROP COUNTER AND CONTROL SYSTEM FOR IRRIGATION SYSTEMS

BACKGROUND—FIELD OF INVENTION

This invention relates to an optical space and velocity monitoring precipitation sensor, combined with an electronic circuit to control automated irrigation or home automation systems.

BACKGROUND—DESCRIPTION OF PRIOR ART

It is generally agreed that, in principle, the use of rain sensing devices provides significant water savings with irrigation systems when properly installed and maintained. However, most rain sensing devices are unreliable, difficult to install, and require periodic maintenance. These disadvantages, combined with an obtrusive physical appearance, have made many irrigation professionals reluctant to install them.

Although the invention can be applied in a variety of contexts, that is, to control or override any automated system that benefits from the ability to respond to the detection of the presence, and subsequent absence, of precipitation, the described invention relates to a precipitation-activated control system that integrates with programmable irrigation systems. This invention automatically disables an irrigation system for user-selectable periods of time related to the opto-electric detection of precipitation. While the current invention is not limited only to the detection of rain, reference to all forms of precipitation henceforth will be as either rain, rainfall, raindrops, or precipitation.

There are a number of systems which override a programmable irrigation system when a specific amount of rainfall is detected. Examples of such systems are disclosed in U.S. Pat. Nos. 4,613,764, 5,321,578, and 5,355,122. All of these patents describe systems that employ a collection container to detect the presence of rainfall. In each, conductive sensors extend down into a rainwater collection container at either a fixed or an adjustable depth from the bottom. The electronics are activated when rainwater reaches the sensors and acts as an electrical connection. The electrical connection of the sensors causes the electronics of the rainfall sensor to isolate the programmable controller from the irrigation valves, or pump start relay. The normal irrigation cycles are thereby interrupted until the rainwater in the collection container evaporates.

In the prior art, the amount of rainwater necessary to interrupt the normal irrigation cycle changes as debris builds up in the collection container. Rain sensors such as U.S. Pat. Nos. 4,613,764 and 5,321,578 are also susceptible to fluctuations in water levels due to high wind conditions. When such conditions exist the collected water can move from side to side, causing an intermittent bridging of the sensors. As a result, rapid switching due to repeated intermittent bridging of the sensors can damage a pump start relay associated with some irrigation systems. Furthermore, high wind conditions may result in water being blown out of the collection container, thereby reducing the overall time delay of the device.

Mechanical precipitation detection and control systems such as U.S. Pat. No. 3,808,385 utilize moisture absorptive disks in an enclosed body that depress a switch when a predetermined amount of precipitation swells the disks. The system remains inactive until the disks dry and shrink releasing the switch. This type of precipitation switch requires at least 1/8" of rainfall to disable the irrigation systems and can allow the system to operate during light rain. Additionally, this type of switch gives the user little control over the shut-off duration after rainfall, and requires a secondary switch to bypass the sensor, if so desired.

The limitations associated with ground moisture sensors are numerous, such as with U.S. Pat. Nos. 5,445,176 and 5,060,859. These systems require an involved installation procedure of burying them at the proper depth related to the base of the root system for the plant material you wish to irrigate. Due to variation of drainage throughout the landscaped region, multiple sensors are usually required at various locations for accurate operation. Because of the nature of the design (i.e: a probe surrounded by soil material), any fallen moisture must first soak into the soil material before the system can detect it. This in itself eliminates the ability to quickly detect the presence of precipitation, not to mention the absence of precipitation after it has first been detected.

Electro-optical rain detectors such as U.S. Pat. Nos. 4,701,613 and 4,987,296 and foreign No. 61-231439 are examples of systems that use a beam of modulated light to detect the presence and amount of precipitation. When a raindrop interrupts the beam of light from an emitter to detector the modulation level decreases, and the amount of change is then used to mathematically calculate the size of the raindrop. These particular sensors use complex circuitry to calculate the size of raindrops, and are designed specifically for automotive use.

OBJECTS AND ADVANTAGES

Accordingly, besides the objects and advantages of the precipitation detection and control system described in the above patents, several objects and advantages of the present invention are:

(a) to provide a precipitation detection and control system with a small waterproof outdoor probe that is extremely sensitive to precipitation without retaining any moisture whatsoever;

(b) to provide a precipitation detection and control system with an outdoor probe that is aesthetically unobtrusive and can be painted or otherwise customized to match its surroundings;

(c) to provide a precipitation detection and control system that requires virtually no maintenance;

(d) to provide a precipitation detection and control system that remains in a passive state until the detection of a single raindrop, at which time the system becomes activated and begins monitoring the intensity of precipitation;

(e) to provide a precipitation detection and control system that utilizes a plurality of electronic precipitation counters that count the number of raindrops during a specified timing cycle;

(f) to provide a precipitation detection and control system that, once activated, if it detects a predetermined number of raindrops during the timing cycle, will activate the output function;

(g) to provide a precipitation detection and control system that if the precipitation counting circuit fails to count a predetermined number of raindrops during a timing cycle it will reset the counter and begin counting again;

(h) to provide a precipitation detection and control system that utilizes a plurality of electronic timers to count timing cycles without precipitation after precipitation has first been detected;

(i) to provide a precipitation detection and control system that, once rainfall stops and if the detected rain duration is shorter than a predetermined period and a predetermined number of timing cycles pass without the detection of precipitation, will deactivate the output function and reset the system to a passive state;

(j) to provide a precipitation detection and control system that, once the detected rain duration is longer than a predetermined time, will reprogram the output delay from a short delay to a user-selectable long delay.

(k) to provide a precipitation detection and control system that allows the user to manually reset the output function and restore normal operations to the controller;

(l) to provide a precipitation detection and control system that allows the user to select either a normally open, normally closed, or logic-level output function;

(m) to provide a precipitation detection and control system that allows the user a plurality of sensitivity selections that electronically vary the triggering threshold for precipitation;

(n) to provide a precipitation detection and control system that does not require any electrical adjustment for ambient background light levels;

(o) to provide a precipitation detection and control system that, upon the interruption of electrical power to the invention, will remain inactive;

(p) to provide a precipitation detection and control system with a power-on reset function that enables it to remain inactive upon the application of power.

(q) to provide a precipitation detection and control system that will not trigger upon the detection of non-repetitive events, such as those caused by an insect, or the like.

Further objects and advantages are to provide a precipitation detection and control system that will easily integrate with virtually any type of automated device benefiting from the ability to respond to the presence and subsequent absence of rainfall and to give the user fully automated operations in any weather condition. Further objects and advantages will become apparent from a consideration of the ensuing description and drawings.

DESCRIPTION OF THE DRAWINGS

The previous aspects, as well as other aspects, of the invention will become more apparent to those skilled in the art from the following disclosure and accompanying figures.

DESCRIPTION OF THE PREFERRED EMBODIMENTS

Figure 1:
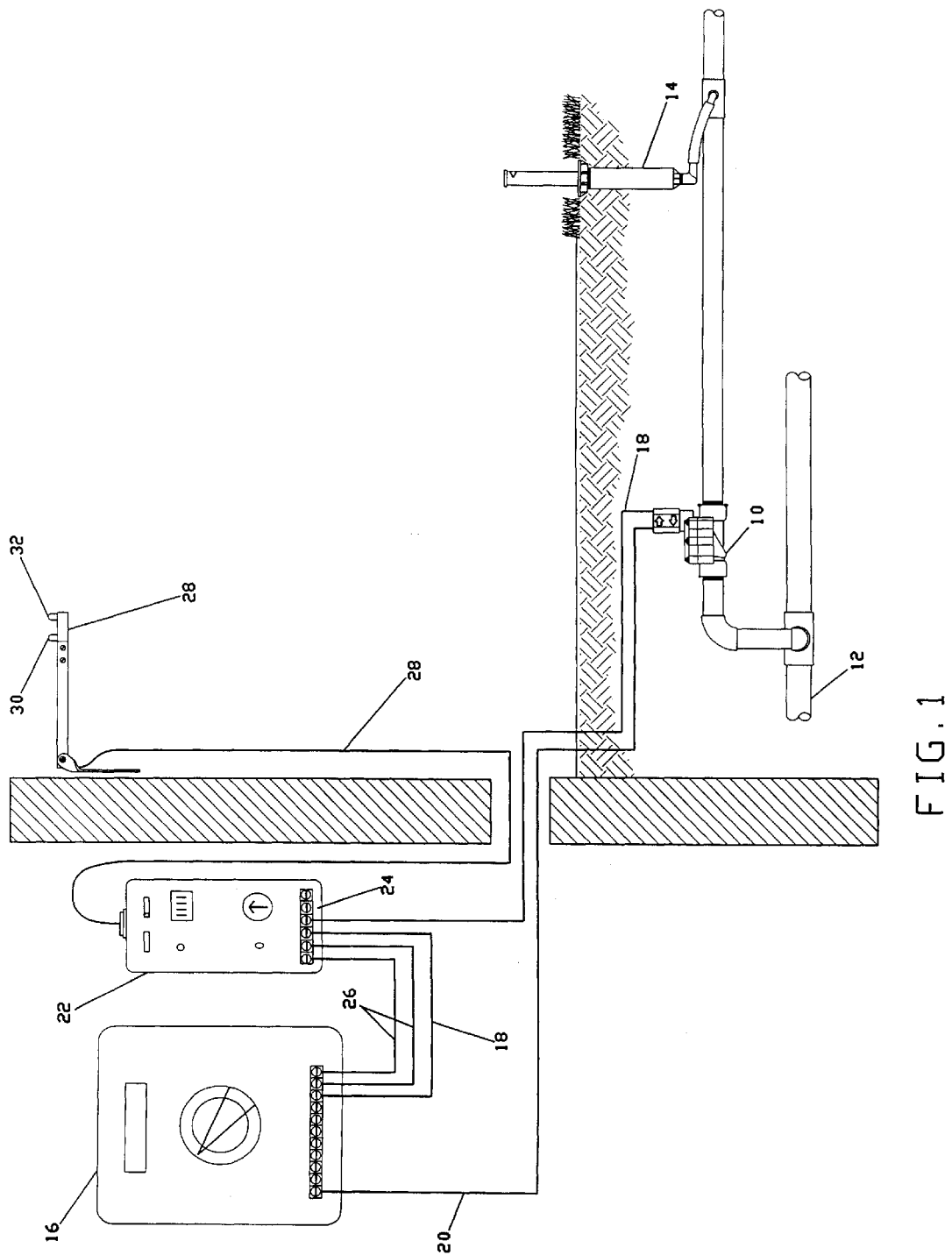
FIG. 1 is an elevated view of a typical irrigation system having a raindrop counter and control system installed, particularly illustrating the outdoor detection probe and the control unit connected to said detection probe and to various electrical components of said irrigation system.

A typical irrigation system, such as described in FIG. 1 has at least one normally closed electrically actuated solenoid valve 10 connected to a pressurized water supply 12 to provide regulated and timed amounts of water through sprinkler heads 14 and the like to a desired plant material.

As shown in FIG. 1, the timing of the actuation of the valves 10 and the subsequent application of water to plant material through sprinkler heads 14 is regulated by an automatic irrigation controller 16. Such a controller 16 is basically an automated timing device that allows the user to select the duration and time of day for watering which is known as a "cycle." Each sprinkler head 14 or group of heads connected to a valve 10 is known as a "zone." The controller 16 sends a 24VAC control signal to each valve 10 for each zone which then remains open for the duration of said cycle, and is repeated throughout each of the zones. Each valve 10 for each zone is connected with a common ground wire 18 and a separate control wire 20 so that all zones can be deactivated (or overridden) by opening the common ground wire 18.

FIG. 1 also shows a typical enclosure for the raindrop counter and control unit 22, mounted in proximity to the irrigation controller 16. A connection block 24 attached to the control unit 22 provides connections for power leads 26 to the 24VAC power available from the irrigation controller 16, or from another power source (not shown).

FIG. 1 further illustrates an outdoor rain detection probe 28 that receives operating voltage from the control unit 22 and supplies an output based on the detection of rainfall via the use of the infrared emitter 30 and detector 32 pair. Power to probe 28, and output signals from said probe to control unit 22, are carried by a multiple conductor cable 34.

Figure 2:
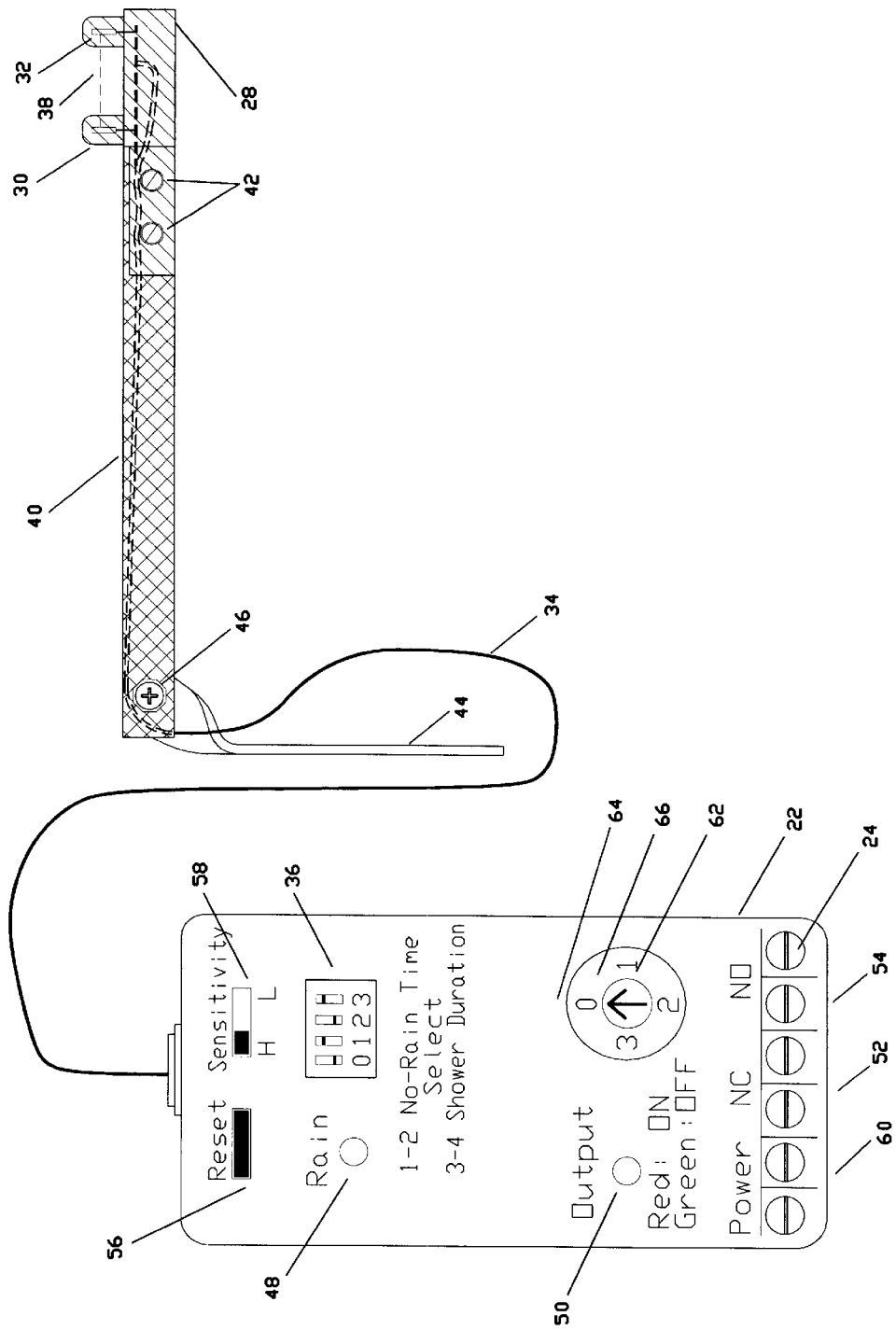
FIG. 2 is a perspective view of an embodiment of the raindrop counter and control unit and an outdoor detection probe in accordance with the present invention.

FIG. 2 illustrates the details of the detection probe 28 and control unit 22. The detection probe 28 is formed in a way to mortise inside a channeled support structure 40 and is secured using weather resistant fasteners 42. The channeled support structure 40 is of a length sufficient to extend the detection probe 28 past any overhanging structural element. A mounting bracket 44 is attached to channeled support structure 40 via a weather resistant fastener 46. The detection probe 28 can be mounted with or without the channeled support structure 40 and mounting bracket 44, giving the user a plurality of mounting possibilities.

As shown in FIG. 2 the control unit 22 includes a rainfall indication LED 48 to give the user "real time" indication of rainfall. When rainfall interrupts the infrared beam 38 produced from the infrared emitter 30 to the detector 32 in the detection probe 28, the rainfall indication LED 48 will briefly illuminate. A continuous illumination of the LED 48 indicates an obstruction of the infrared beam 38 or a disconnection of the multiple conductor cable 34.

FIG. 2 also illustrates that when a predetermined number of raindrops are detected by the detection probe 28, the output function of the control unit 22 will become activated as indicated by the color of the output indicator LED 50, which will change from green indicating an inactive state, to red indicating the output function is active. Normally closed 52, or normally open 54, output terminals are user selected on connection block 24. Other automated devices (not shown) may require a normally open output 54, such as controllers with dedicated sensor inputs or devices that require activation in the event of rain. A push button reset switch 56 allows the output function of control unit 22 to be reset to an inactive state, in the event that service is required to the irrigation system shortly after rainfall, or if otherwise desired.

FIG. 2 also shows the sensitivity to rainfall is adjustable to a plurality of settings via the sensitivity switch 58, which changes the triggering threshold voltage allowing the invention to either ignore or detect light rain. In addition, power to the control unit 22 is provided by power terminals 60 that connect to either the 24VAC power available from the controller 16, or a separate power supply (not shown).

Furthermore, as shown in FIG. 2 the duration of delay in reactivating the irrigation system after rainfall is user selectable through the delay switch 62. With the selection of the zero delay setting 64, the device will return to a passive state and will reset the output function within minutes of detecting the absence of rainfall. If the user selects one of a plurality of timed delay settings 66, the irrigation system will remain inactive until the completion of said delay setting. A shower duration threshold setting 36 allows the device to reset if the measured duration of rainfall is less than the user selected setting. If the measured duration of rainfall is greater than the user selected setting, the system remains inactive for the duration of the timed delay.

Figure 3:
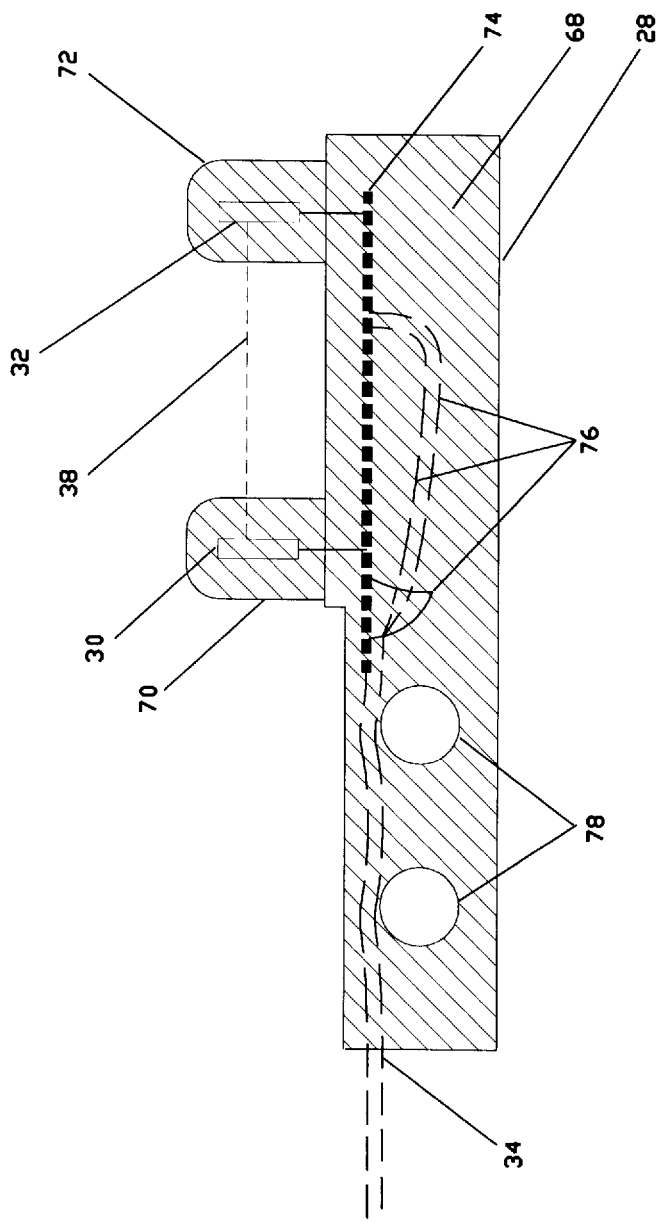
FIG. 3 is a perspective view of an embodiment of the outdoor detection probe in accordance with the present invention as shown in FIG. 2.

FIG. 3 of the drawings illustrates an outdoor precipitation detection probe assembly 28 in accordance with the present invention, which is mounted directly to a gutter or other outdoor structure of a residential or commercial building (not shown). An optional support structure 40 and mounting bracket 44, as illustrated in FIG. 2 allows the user further mounting options.

As shown in FIG. 3, the outdoor detection probe 28 comprises a solid molded or cast element 68 of Lexan-™, or similar material, tinted with a colorant transparent to near infrared light, such as GE # 52125 or the like. An infrared emitter element 30 is disposed within a protuberance of said material 70, while a light receiving element 32 is disposed within a second protuberance of the same material 72. Such an arrangement of the electro-optical elements allows a beam of infrared light 38 to pass freely between the protuberances 70 and 72, permitting precipitation to freely pass between said protuberances and through said beam. The interruption of the beam 38 will be detected by the control unit 22 described in FIG. 1, without the retention of any moisture. Within said detection probe 28, the electro-optical elements 30 and 32 are mounted at a fixed distance on a printed circuit board 74 before being molded or cast into said material 68.

In manufacture of the outdoor detection probe 28 the component parts could be assembled as follows:
1. The infrared emitter 30, detector 32 and individual cable leads 76 from the multiple conductor cable 34 are all soldered to connecting traces on a printed circuit board 74 to produce a single unit.
2. The detection unit 28 is then cast or injection molded to form a solid structure of material, tinted with a colorant transparent to near infrared light, comprising twin protuberances to produce a single plastic structural element. A plurality of mounting cavities, such as cavities 78 can be added or omitted to allow for various mounting options.
3. An optional process of shielding or masking the inside surface area of each protuberance 70, 72 will allow the unit to be painted. After painting, the masking is removed to reveal opposing openings in the painted surface that allow light to pass between the electro-optical elements 30, 32. Such painting will allow the detection probe 28 to match the surrounding structure to which it is mounted and become visually unobtrusive.

The above mentioned and other objects of the invention are accomplished as described in the continuing sections.

Figure 4A:
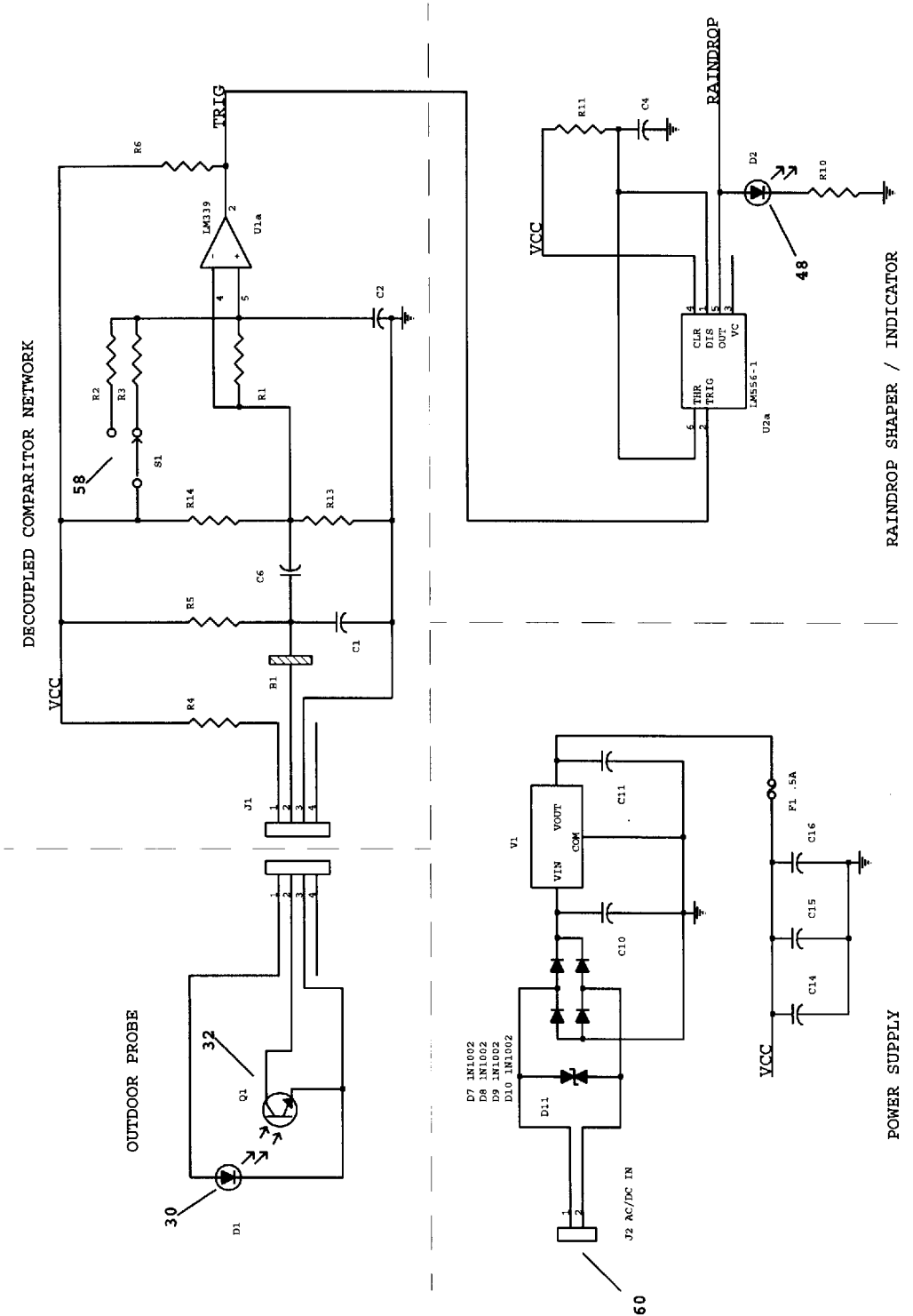
FIG. 4A,4B,and 4C are schematic diagrams illustrating the operation of the analog and digital functions of the present invention.
Figure 4B:
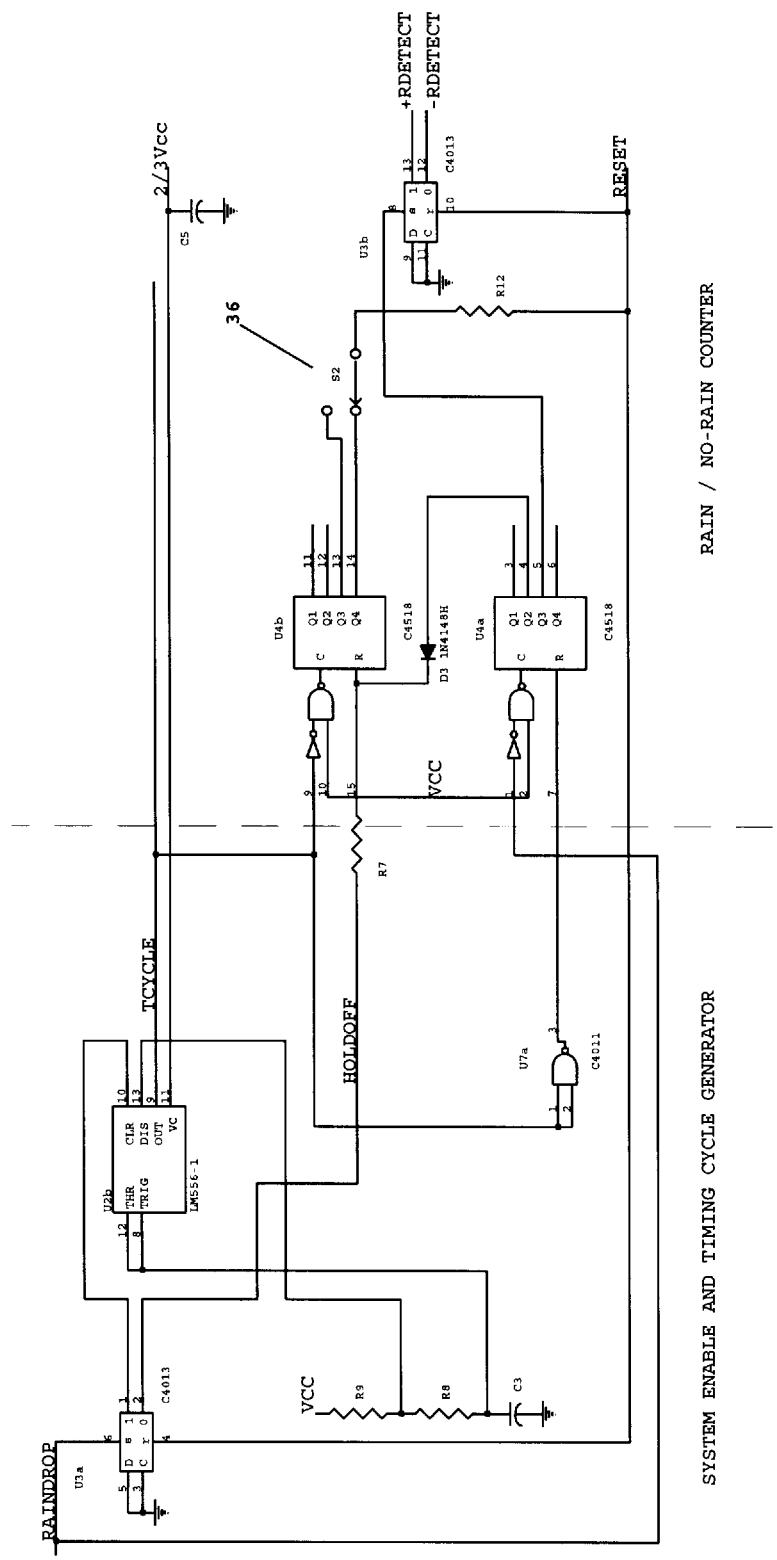
Figure 4C:
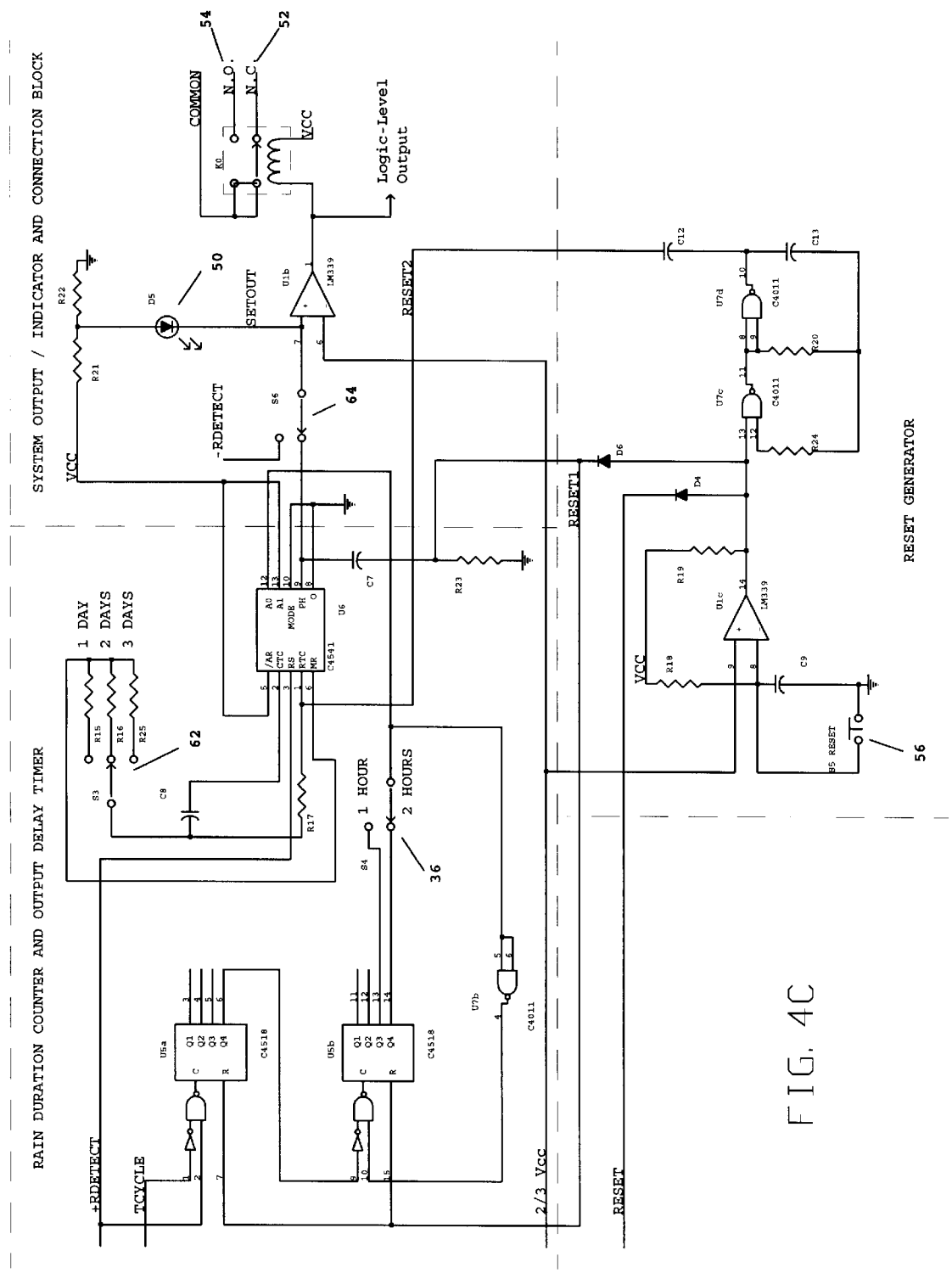
Figure 5:
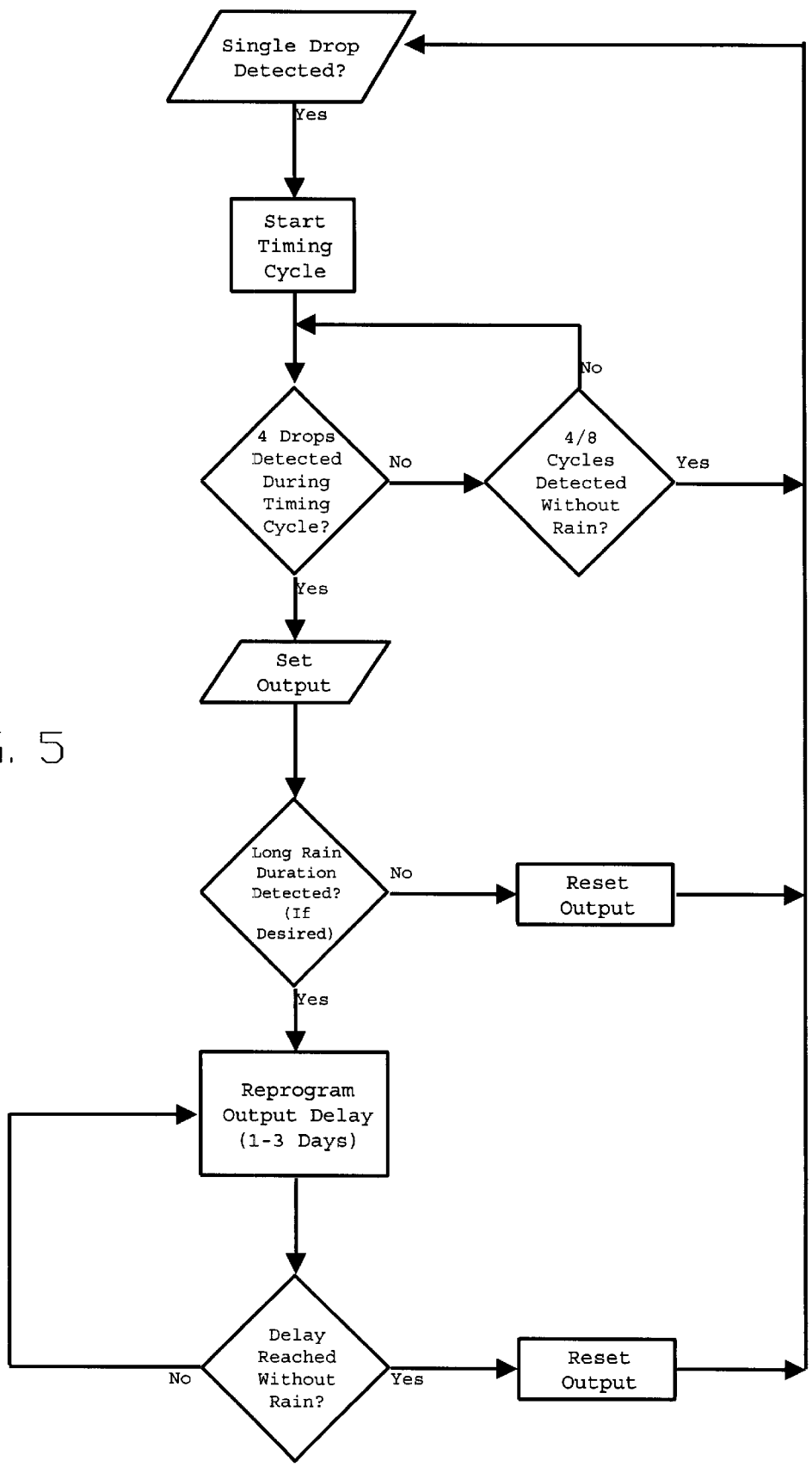
FIG. 5 is a system flow chart illustrating the system algorithm from the detection of a single raindrop to the activation of the output function of the present invention.
Figure 6:
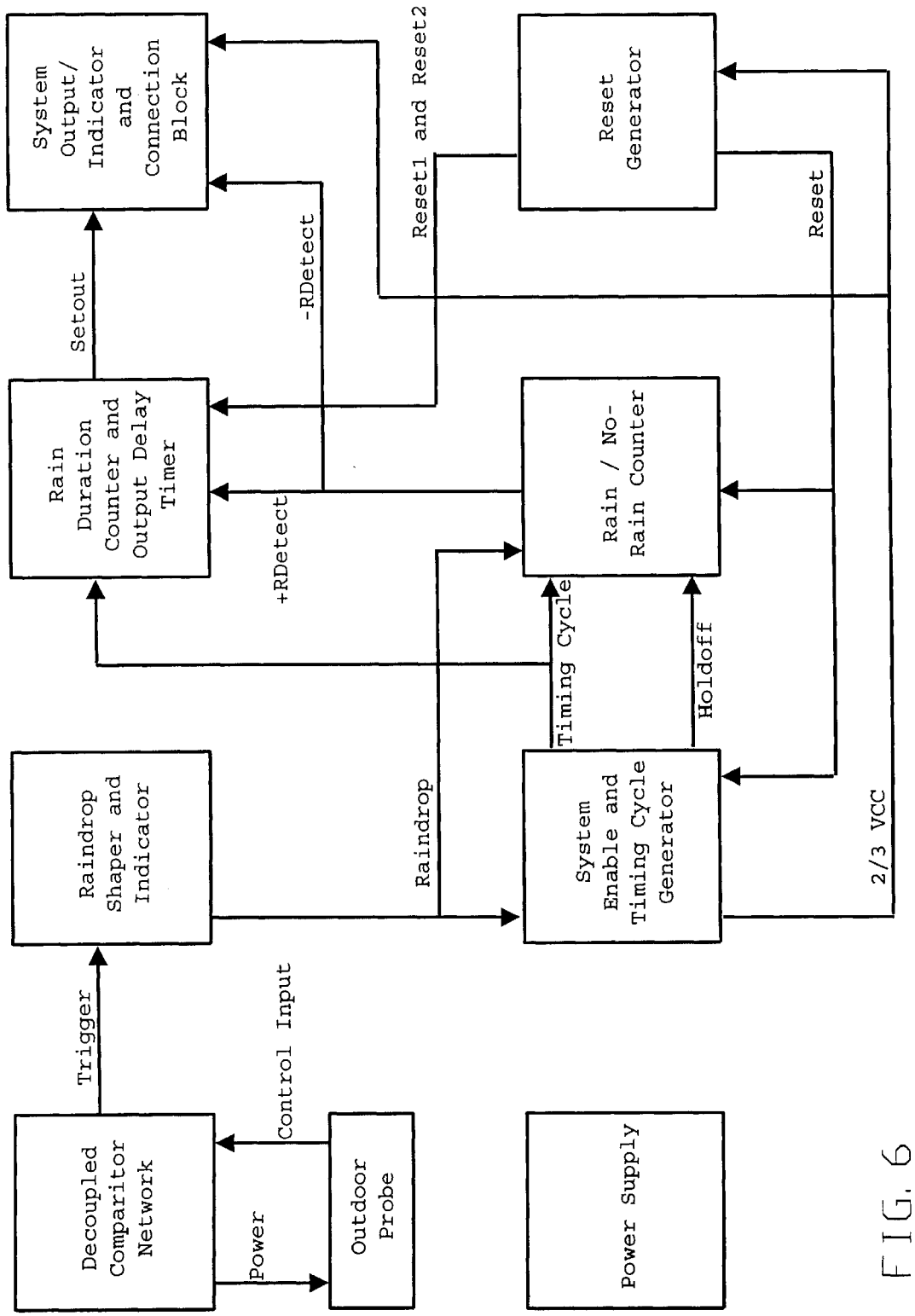
FIG. 6 is a diagram of the block functions of the invention.

Operation—FIGS 4A, 4B and 4C.

In FIG. 4A the power input for the invention is a multi-voltage system using a full-wave bridge rectifier created by diodes D7–D10, voltage regulator V1, and capacitors C10 and C11. By using a full-wave rectifier, voltage regulator, and adequate filter capacitance, the input power can be either 24VAC 26 or DC voltage from 15V to 28V. The system is protected from minor power surges by the transient voltage suppresser D11. The multi-voltage input allows the invention to be used with all 24VAC sources available from commercial or residential irrigation controllers, or from a variety of power supply's easily obtainable through many retail sources and connected without regard to proper polarity.

A direct beam of infrared light 38 is passed from the infrared emitter D1 30 to the detector Q1 32. When a raindrop passes through the IR beam 38 it is momentarily interrupted, resulting in an increase in voltage on the output of the detector Q1 32. This increase in voltage is detected by the comparator U1:$a$.

Comparator U1:$a$ is used as the means to detect rainfall, and utilizes a decoupled comparator network designed to react only to quick changes in detected light while ignoring slow changes. Any incidental light present such as sunlight, automobile headlights, streetlights, etc., causes variations in the output voltage of detector Q1 32. Decoupling capacitor C6 will isolate these slow changes from the comparator while allowing quick changes to pass through. The network is then biased at ½ Vcc by resistors R13 and R14. The reference pin of U1:$a$ is connected back to the inputvoltage through R1, and is also connected to the network of C2, and one of the resistors (R2 or R3) selected by switch S1 58 which is used to allow control over the triggering threshold to precipitation. In addition to ignoring slow changes due to ambient light fluctuations, the decoupled network also performs another valuable function of eliminating any manual adjustment of the unit, either by the user at time of installation or by the manufacturer during assembly, to compensate for ambient light levels at the location of use, or due to variations in electrical component characteristics or the manufacturing process itself.

When an interruption in the IR beam 38 is detected, the rapid increase in output voltage of detector Q1 32 results in the output of comparator U1:$a$ being driven to a logic low which in turn triggers timer U2:$a$. Timer U2:$a$ is used to shape the detected raindrop into an accurate positive pulse, indicated by a brief illumination of light emitting diode D2 48.

In FIG. 4B the first such pulse is used to activate the system by 'setting' the Q output of DFF U3:$a$. This in turn activates a free-running astable timer U2:$b$, used to generate the main timing cycle for the entire system (approximately 60 seconds) and is based on the time constant of RC network R8, R9, and C3. This timing cycle is used not only as a means to determine the intensity of rainfall, but also as a means to detect the absence of rainfall.

When timer U2:$b$ becomes activated by the detection of a single raindrop, it enables a pair of counters: U4:$a$ and U4:$b$. U4:$a$ will be referred to as the 'rain' counter and U4:$b$ will be referred to as the 'no-rain' counter. If, after the initial raindrop activates the counters, four additional raindrops are counted during the period of 1 timing cycle, the Q3 output of the rain counter will go to a logic high, which in turn will 'set' DFF U3:$b$ and generate the signals known as +RDETECT and −RDETECT. If, however, less than 4 raindrops are counted during the period of 1 timing cycle, the rain counter will be reset and will begin counting again from zero at the beginning of the next timing cycle.

Once rainfall is detected, and if it continues to fall, the rain counter output Q2 will continually reset the no-rain counter. However, when rain ceases, the rain counter, no longer counting raindrops, discontinues resetting the no-rain counter, which will then detect the absence of rain by counting the number of timing cycles without rain. When the no-rain counter reaches a preselected count without rain it 'resets' DFF U3:a and U3:b, which removes the +/−RDETECT signals, disables the timing cycle, and resets the rain and the no-rain counters. The number of timing cycles required to initiate this action is selected by switch S2 36.

In FIG. 4C the output section of the invention is designed with several unique features. First and foremost, it will rapidly indicate the presence of rainfall. It will then determine the duration of the rainfall and program the output delay based on the sensed duration of rainfall, if so desired. Both the sensed duration required to reprogram the delay, and the delay itself, are user selectable. These features are accomplished by the use of programmable timer U6, and 2 rain-duration counters U5:a and U5:b, which are connected such that they are used as a single 8-stage counter with separate enable inputs for the upper 4 and lower 4 stages.

Immediately upon sensing the +RDETECT signal, the output of programmable timer U6 is driven to a logic low, changing the bicolor output indicator D5 50 from green to red (indicating precipitation has been detected) and driving the output of comparator U1:b low activating relay K1, which controls the NO 54 and NC 52 SPST switched output of the invention. (The output of comparitor U1:b or U6 can also be used directly as a logic-level output.) Once the programmable timer has sensed the +RDETECT signal it will remain activated for the duration of the signal, and then, after the removal of the signal until the end of a delay count determined by the clock frequency adjusted by the RC network of C8, R17, and one of resistors R15, R16, or R25, which are selected by switch S3 62. The true use of this circuit will become evident upon consideration of the continued description.

The presence of the +RDETECT signal also enables the lower 4 stages of the rain-duration counter U5:a. The rain-duration counter will determine the duration of precipitation by counting the number of timing cycles with detected rainfall. If the rain-duration counter counts the preselected number of timing cycles with rainfall, it reprograms timer U6 from a short delay count (1024) to a long delay count (65536) while simultaneously disabling the upper 4 stages of the counter (U5:b) effectively latching the reprogram function until the timer completes its entire long delay count. This reprogramming is done after either 56 or 120 timing cycles, chosen via switch S4 36 and toggles timer program pin A0 of U6. Furthermore, the long delay count time period is selectable via switch S3 62 to allow adjustment from one to several days. The use of discrete resistors and switch S3 62 as opposed to a variable potentiometer, will eliminate routine cleaning of the potentiometer if exposed to a dirty or otherwise hostile environment, and will also allow accurate adjustment of the long delay time period without experimentation to determine the desired setting.

Once the timer has completed its programmed time delay count, either short or long, the output toggles to a logic high changing bicolor output indicator D5 50 from red to green, indicating the invention is in an inactive state, deactivating relay K1, and resetting the rain-duration counters.

If so desired, relay K1 can be directly controlled by the −RDETECT signal using the zero delay setting switch S6 64 effectively bypassing the programmable timer and the rain-duration counter. This function will be used by systems requiring the immediate detection of the presence and subsequent absence of rainfall.

Complete system reset functions are performed by U1:c, and U7:c and U7:d combined as a single voltage controlled oscillator. U1:c is a comparator used to generate the main reset pulse. It is referenced at ⅔ Vcc and the input is tied to an RC network comprised of R18 and C9. When power is first applied, the output of comparator U1:c will go to a logic high for a short duration until the voltage on C9 charges to ⅔ Vcc. The output of comparator U1:c will then toggle to a logic low, where it will remain until power is interrupted and again restored. This reset pulse will reset the rain-duration counter U5:a and U5:b, DFF U3:b, and DFF U3:a which in turn resets the timing cycle U2:b, both the rain and no-rain counters U4:a and U4:b. It also enables the reset oscillator U7:c and U7:d. The reset oscillator is designed to create a high frequency clock signal to quickly clock programmable timer U6 through its entire timing delay cycle, effectively resetting the output to a logic high. This reset function will serve to insure the output of the invention becomes inactive upon the application of power. The input of comparator U1:c is also tied to momentary switch S5 56 which, once pressed by the user, will also initiate the reset function allowing manual reset of the system.

The invention has been described in detail with particular reference to an illustrative preferred embodiment thereof, but it will be understood that variations and modifications can be effected within the spirit and scope of the invention as described above and as defined in the appended claims.

SUMMARY, RAMIFICATIONS, AND SCOPE

The present invention overcomes the deficiencies in the prior art by providing a raindrop counter and control system that utilizes an optical detection method that eliminates the need to collect any moisture, and easily integrates with a plurality of time programmable systems, including, but not limited to, irrigation systems. This elimination of collected moisture removes variables associated with those types of devices, such as inconsistent drying characteristics under different conditions, movement of water in the collection container, or the inability to detect the absence of precipitation after it has first been detected. By making an irrigation system responsive to natural precipitation as required by the user, the system acts to supplement rainfall only when needed, thus promoting the healthy growth of plant material and prevents the waste of water. Furthermore, the raindrop counter and control system has additional advantages in that

- it provides a small waterproof outdoor probe that is extremely sensitive to precipitation without retaining any moisture whatsoever;
- it provides an outdoor probe that is aesthetically unobtrusive and can be painted or otherwise customized to match its surroundings;
- it provides a raindrop counter and control system that requires virtually no maintenance;
- it provides a raindrop counter and control system that once activated, will activate the output funcion if it detects a predetermined number of raindrops during the timing cycle;
- it provides a raindrop counter and control system that once rainfall stops, and a predetermined number of timing cycles pass without the detection of precipitation (if a long delay was not selected), will deactivate the output function and reset the system to a passive state;
- it provides either a logic-level, normally open, or normally closed output to interface with a plurality of systems.

Although the descriptions and operations above contain many specificities, these should not be considered as limiting the scope of the invention but as providing an illustration of the presently preferred embodiment. For example, the outdoor probe can take many shapes; the protuberances that contain the emitter and detector can be cast separately or as one; the probe could be cast to resemble a structural element of a building to which it is mounted; the control unit could be made weatherproof so that the entire unit could be mounted in proximity to outdoor irrigation controllers; the logic functions of the system could be achieved using a microprocessor and software, or the functions could be fabricated into one integrated circuit. Thus the scope of the invention should be determined by the appended claims and their legal equivalents, rather than by the examples given.

Drawing Reference Numerals Worksheet

Part Name

| | |
|---|---|
| 10 | Solenoid valve |
| 12 | Pressurized water supply |
| 14 | Sprinkler heads |
| 16 | Automatic irrigation controller |
| 18 | Common ground wire |
| 20 | Control wire |
| 22 | Control unit |
| 24 | Connection block |
| 26 | Power leads |
| 28 | Rain detection probe |
| 30 | Infrared emitter |
| 32 | Infrared detector |
| 34 | Multiple conductor cable |
| 36 | No-rain time selector and shower duration selector |
| 38 | Infrared light beam |
| 40 | Channeled support structure |
| 42 | Weather resistant fasteners |
| 44 | Mounting bracket |
| 46 | Weather resistant fastener |
| 48 | Rainfail indication LED |
| 50 | Output indicator LED |
| 52 | Normally closed output terminals |
| 54 | Normally open output terminals |
| 56 | Reset switch |
| 58 | Sensitivity switch |
| 60 | Power input terminals |
| 62 | Delay switch |
| 64 | Zero delay setting |
| 66 | Timed delay settings |
| 68 | Cast element |
| 70 | Protuberance of cast material |
| 72 | Second protuberance of cast material |
| 74 | Printed circuit board |
| 76 | Cable leads |
| 78 | Cavities |

What is claimed is:

1. A raindrop counter and control system for overriding a plurality of automated devices requiring the ability to detect the presence, subsequent absence, and duration of precipitation, which comprises:
   (a) An outdoor rain sensor containing a single pair of opposing mounted Infrared (IR) emitter and detector connected to a separate control unit via a multi-conductor cable such that the emitter receives power from the control unit via a conductor, and a separate conductor connected to the collector of the IR detector sends a signal back to the control unit,
   (b) a separately mounted control unit connected to said outdoor probe which supplies a current limited voltage through resistor R4 to the IR emitter which produces a beam of IR light which will be detected by the IR detector thus creating a control voltage on the collector pin of the detector which is connected, via a conductor within the multi-conductor cable, to the input pin of comparator U1a through capacitor C6,
   (1) the control signal also being tied to resistor R1, the opposite end of resistor R1 being tied to the reference input of comparator U1a, which is then held steady by capacitor C2, whereby, any quick positive change in the input voltage of comparator U1a will be detected resulting in a logic-low pulse on the output of the comparator,
   (2) the offset voltage between the input pin and reference pin of comparator U1a being selectable via the switched resistor network of resistors R2 and R3 allowing selectable levels of sensitivity,
   (3) the output of comparator U1a being tied to the trigger pin of timer U2a, where a logic-low pulse will trigger the timer and supply a logic-high pulse to the output of timer U2a for approximately 100 mS, the duration being determined by the time constant set by resistor R11 and capacitor C4,
   (4) the output of timer U2a being tied to the set pin of DFF U3a, where a logic-high pulse will result in a logic-high being applied to the Q output of DFF U3a causing timer U2b to begin a timing cycle of approximately 60 seconds, determined by the time constant of resistors R8, R9, and capacitor C3,
   (5) the output of timer U2b is tied to the input pins of an inverter created with NAND gate U7a, where a logic-high will apply a logic-low to the output of the inverter removing the reset signal applied to counter U4a, thus enabling the counter,
   (6) the output of timer U2a is also tied to the clock pin of counter U4a, which, once enabled by the removal of the reset signal from inverter U7a, will begin counting the number of raindrops,
   (c) contain an electronic control circuit having the means to use the number of counted raindrops to detect the presence of precipitation, the subsequent absence of precipitation, determine the duration of detected precipitation,
   (d) contain circuitry to provide visual display of both the active or passive status of the unit and the detection of individual raindrops, and allow selection of the output mode of the unit, either logic-level, normally open (N.O.), or normally closed (N.C.).

2. A raindrop counter and control system for overriding a plurality of automated devices requiring the ability to detect the presence, subsequent absence, and duration of precipitation, which comprises:
   (A) An outdoor rain sensor containing a single pair of opposing mounted Infrared (IR) emitter and detector connected to a separate control unit via a multi-conductor cable such that the emitter receives power from the control unit via a conductor, and a separate conductor connected to the collector of the IR detector sends a signal back to the control unit,
   (B) a separately mounted control unit connected to said outdoor probe which supplies a current limited voltage through resistor R4 to the IR emitter which produces a beam of IR light which will be detected by the IR detector thus creating a control voltage on the collector pin of the detector which is connected, via a conductor within the multi-conductor cable, to the input pin of comparator U1a through capacitor C6, (1) the control signal also being tied to resistor R1, the opposite end of resistor R1 being tied to the reference input of comparator U1a, which is then held steady by capacitor C2, whereby, any quick positive change in the input voltage of comparator U1a will be detected resulting in a logic-low pulse on the output of the comparator, (2) the offset voltage between the input pin and reference pin of comparator U1a being selectable via the switched resistor network of resistors R2 and R3 allowing selectable levels of sensitivity, (3) the output of comparator U1a being tied to the trigger pin of timer U2a, where a logic-low pulse will trigger the timer and supply a logic-high pulse to the output of timer U2a for approximately 100 mS, the duration being determined by the time constant set by resistor R11 and capacitor C4, (4) the output of timer U2a being tied to the set pin of DFF U3a, where a logic-high pulse will result in a logic-high being applied to the Q output of DFF U3a causing timer U2b to begin a timing cycle of approximately 60 seconds, determined by the time constant of resistors R8, R9, and capacitor C3, (5) the output of timer U2b is tied to the input pins of an inverter created with NAND gate U7a, where a logic-high will apply a logic-low to the output of the inverter removing the reset signal applied to counter U4a, thus enabling the counter, (6) the output of timer U2a is also tied to the clock pin of counter U4a, which, once enabled by the removal of the reset signal from inverter U7a, will begin counting the number of raindrops, (C) contain an electronic control circuit where:

(a) the Q3 output of counter U4a is tied to the set pin of DFF U3b, and once a pre-determined count of raindrops is reached, will become a logic-high which in turn will cause the Q output pin of DFF U3b to become a logic-high indicating rain has been detected, (1) the Q output of DFF U3b being connected to the master reset of programmable timer U6 where the application of a logic-high activates the timer causing the output pin to be driven to a logic-low, (2) the output pin of timer U6 is tied to the input pin of comparator U1b, the reference pin of comparator U1b is connected to $2/3$ Vcc supplied by U2b, where a logic-low applied to the input pin will result in a logic-low on the output pin, activating the relay K1, (b) the clock pin of counter U4b is tied to the output of the timing cycle generator U2b, the purpose of U4b being to count the number of timing cycles, (1) the Q2 output of counter U4a is tied, through diode D3, to the reset pin of counter U4b, which will continually reset counter U4b provided rain is continually detected, but, once rain ceases to fall, timer U4b is allowed to count the number of timing cycles without detected rain, (2) the Q3 or Q4 output of timer U4b, selected via switch S2, is tied to the reset pin of DFF U3b, which will cause DFF U3b to be reset once the preselected number of timing cycles without rainfall is reached, thereby returning the Q output of DFF U3b to a logic-low, indicating the detection of the absence of rainfall, (c) the clock pin of the first stage of cascaded counters U5a and U5b being tied to the output pin of the timing cycle generator U2b, (1) the Q output of DFF U3b being tied to the clock enable pin of the first stage of cascaded counters U5a and U5b, which, once rainfall is detected, will begin counting timing cycles thereby allowing the detection of the duration of rainfall, (D) contain circuitry to provide visual display of both the active or passive status of the unit and the detection of individual raindrops, and allow selection of the output mode of the unit, either logic-level, normally open (N.O.), or normally closed (N.C.).

3. A raindrop counter and control system for overriding a plurality of automated devices requiring the ability to detect the presence, subsequent absence, and duration of precipitation, which comprises:

(A) An outdoor rain sensor containing a single pair of opposing mounted Infrared (IR) emitter and detector connected to a separate control unit via a multi-conductor cable such that the emitter of the sensor receives power from the control unit via a conductor, and a separate conductor connected to the collector of the IR detector sends a signal back to the control unit, (B) a separately mounted control unit connected to said outdoor probe which supplies a current limited voltage through resistor R4 to the IR emitter which produces a beam of IR light which will be detected by the IR detector thus creating a control voltage on the collector pin of the detector which is connected, via a conductor within the multi-conductor cable, to the input pin of comparator U1a through capacitor C6, (1) the control signal also being tied to resistor R1, the opposite end of resistor R1 being tied to the reference input of comparator U1a, which is then held steady by capacitor C2, whereby, any quick positive change in the input voltage of comparator U1a will be detected resulting in a logic-low pulse on the output of the comparator, (2) the offset voltage between the input pin and reference pin of comparator U1a being selectable via the switched resistor network of resistors R2 and R3 allowing selectable levels of sensitivity, (3) the output of comparator U1a being tied to the trigger pin of timer U2a, where a logic-low pulse will trigger the timer and supply a logic-high pulse to the output of timer U2a for approximately 100 mS, the duration being determined by the time constant set by resistor R11 and capacitor C4, (4) the output of timer U2a being tied to the set pin of DFF U3a, where a logic-high pulse will result in a logic-high being applied to the Q output of DFF U3a causing timer U2b to begin a timing cycle of approximately 60 seconds, determined by the time constant of resistors R8, R9, and capacitor C3, (5) the output of timer U2b is tied to the input pins of an inverter created with NAND gate U7a, where a logic-high will apply a logic-low to the output of the inverter removing the reset signal applied to counter U4a, thus enabling the counter, (6) the output of timer U2a is also tied to the clock pin of counter U4a, which, once enabled by the removal of the reset signal from inverter U7a, will begin counting the number of raindrops, (C) contain an electronic control circuit where:

(a) the Q3 output of counter U4a is tied to the set pin of DFF U3b, and once a pre-determined count of raindrops is reached will become a logic-high which in turn will cause the Q output pin of DFF U3b to become a logic-high indicating rain has been detected, (1) the Q output of DFF U3*b* being connected to the master reset of programmable timer U6 where the application of a logic-high activates the timer causing the output pin to be driven to a logic-low, (2) the output pin of timer U6 is tied to the input pin of comparitor U1*b*, the reference pin of comparitor U1*b* is connected to ⅔ Vcc supplied by U2*b*, where a logic-low applied to the input pin will result in a logic-low on the output pin, activating the relay K1, (b) the clock pin of counter U4*b* is tied to the output of the timing cycle generator U2*b*, the purpose of U4*b* being to count the number of timing cycles, (1) the Q2 output of counter U4*a* is tied, through diode D3, to the reset pin of counter U4*b*, which will continually reset counter U4*b* provided rain is continually detected, but, once rain ceases to fall, timer U4*b* is allowed to count the number of timing cycles without detected rain, (2) the Q3 or Q4 output of timer U4*b*, selected via switch S2, is tied to the reset pin of DFF U3*b*, which will cause DFF U3*b* to be reset once the preselected number of timing cycles without rainfall is reached, thereby returning the Q output of DFF U3*b* to a logic-low, indicating the detection of the absence of rainfall, (c) the clock pin of the first stage of cascaded counters U5*a* and U5*b* being tied to the output pin of the timing cycle generator U2*b*, (1) the Q output of DFF U3*b* being tied to the clock enable pin of the first stage of cascaded counters U5*a* and U5*b*, which, once rainfall is detected, will begin counting timing cycles thereby allowing the detection of the duration of rainfall, (D) provide additional circuitry where:

(a) the output pin of programmable timer U6 is connected to a bicolor LED D5, the opposite end of D5 being tied to resistor R22, the opposite end of R22 being tied to ground, such that a logic-high on the output of programmable timer U6 will result in current flowing through LED D5 illuminating it green, indicating the unit is in a passive state waiting to detect a rain event, (1) LED D5 also being tied to resistor R21, the opposite end of R21 being tied to Vcc, such that a logic-low voltage on the output of programmable timer U6 will result in an opposite current flowing Through LED D5 illuminating it red, indicating the unit has detected rain and is in an active state, (b) the output pin of timer U2*a* is tied to LED D2, the opposite end of D2 being tied to ground through resistor R10, where a logic-high pulse resulting from the detection of a single raindrop will cause the momentary illumination of D2 indicating the detection of each individual raindrop, (c) the output connections, either logic-level, normally open (N.O.), or normally closed (N.C.) are connected to a terminal block and are capable of controlling either logic or power functions allowing connection to a plurality of control units.

* * * * *